United States Patent
Shima et al.

(10) Patent No.: US 6,787,656 B2
(45) Date of Patent: Sep. 7, 2004

(54) CATALYST FOR PRODUCTION OF ETHYLENE OXIDE, METHOD FOR PRODUCTION THEREOF, AND METHOD FOR PRODUCTION OF ETHYLENE OXIDE BY THE USE OF THE CATALYST

(75) Inventors: Masahide Shima, Kawasaki (JP); Hitoshi Takada, Yokohama (JP)

(73) Assignee: Nippon Shokubai Co., Ltd., Osaka (JP)

( * ) Notice: Subject to any disclaimer, the term of this patent is extended or adjusted under 35 U.S.C. 154(b) by 138 days.

(21) Appl. No.: 10/287,969

(22) Filed: Nov. 5, 2002

(65) Prior Publication Data

US 2003/0092922 A1 May 15, 2003

(30) Foreign Application Priority Data

Nov. 6, 2001 (JP) ........................... 2001-340572

(51) Int. Cl.⁷ ............................................. C07D 301/10
(52) U.S. Cl. ......................................... 549/534
(58) Field of Search ......................................... 549/534

(56) References Cited

U.S. PATENT DOCUMENTS

| | | | |
|---|---|---|---|
| 5,055,442 A | 10/1991 | Osaka et al. | ............... 502/439 |
| 5,077,256 A | 12/1991 | Yamamoto et al. | ......... 502/243 |
| 5,100,859 A | 3/1992 | Gerdes et al. | ............... 502/439 |
| 5,145,824 A | 9/1992 | Buffum et al. | ............... 502/216 |
| 5,395,812 A | 3/1995 | Nagase et al. | ............... 502/238 |
| 5,801,259 A | 9/1998 | Kowaleski | ................... 549/536 |

FOREIGN PATENT DOCUMENTS

| | | | |
|---|---|---|---|
| EP | 0 496 386 A1 | 7/1992 | ............ B01J/21/14 |
| EP | 0 496 470 A1 | 7/1992 | ......... C07D/301/10 |
| JP | 2-194839 | 8/1990 | ............ B01J/23/66 |
| JP | 2-290257 | 11/1990 | ............ B01J/35/02 |
| JP | 5-84440 | 4/1993 | ............ B01J/23/68 |
| JP | 5-329368 | 12/1993 | ............ B01J/23/66 |
| JP | 6-47278 | 2/1994 | ............ B01J/23/02 |
| WO | WO 97/40932 | 11/1997 | ............ B01J/21/06 |

*Primary Examiner*—Joseph K. McKane
*Assistant Examiner*—Taofiq A. Solola
(74) *Attorney, Agent, or Firm*—Fish & Richardson P.C.

(57) ABSTRACT

A catalyst for gas phase oxidation of ethylene which excels in selectivity and life performance, a method for the production of the catalyst and a method for the production of ethylene oxide by the use of the catalyst are disclosed. Specifically, the catalyst for the production of ethylene oxide has silver deposited on a carrier containing 90.0–98.9 mass % of α-alumina, 0.01–1 mass % of a compound of at least one metal element selected from the group consisting of potassium and iron (calculated as oxide), 0.1–5 mass % of a silicon compound (calculated as oxide), and 1–5 mass % of zirconium compound (calculated as oxide) in inner portion thereof, the method for the production of this catalyst, and the method for the production of ethylene oxide by the use of this catalyst.

14 Claims, No Drawings

CATALYST FOR PRODUCTION OF ETHYLENE OXIDE, METHOD FOR PRODUCTION THEREOF, AND METHOD FOR PRODUCTION OF ETHYLENE OXIDE BY THE USE OF THE CATALYST

CROSS REFERENCE TO RELATED APPLICATIONS

Pursuant to 35 USC § 119, this application claims the benefit of Japan Patent Application No. 2001-340572 filed Nov. 6, 2001.

BACKGROUND OF THE INVENTION

1. Field of the Invention

This invention relates to a catalyst obtained by depositing a silver component on a carrier containing specific elements and then heat-treating the resultant composite and used for the production of ethylene oxide, a method for the production thereof, and a method for the production of ethylene oxide by the use of the catalyst.

2. Description of the Related Art

Numerous reports covering catalysts to be used for producing ethylene oxide by the gas phase oxidation of ethylene with a molecular oxygen-containing gas and carriers therefor have been heretofore published in literature.

JP-A-06–47278, for example, discloses a catalyst carrier for use in the production of ethylene oxide which comprises at least 85 mass % of α-alumina (calculated as oxide), 0.001–6 mass % (calculated as oxide) of calcium oxide or magnesium oxide, 0.01–5 mass % (calculated as silica) of silicon oxide, and 0–10 mass % (calculated as oxide) of zirconium oxide.

The same patent publication also discloses a method for producing a catalyst carrier for use in the production of ethylene oxide by mixing α-alumina powder of high purity, a calcium compound or a magnesium compound or a magnesium oxide, a silicon compound, and a zirconium compound with water and a binder in specific quantities to give a final carrier containing not less than 85 mass % of α-alumina, extrusion molding the resultant mixture into pellets, and calcining the pellets at a temperature of not lower than 1300° C.

The carrier mentioned above is effective for a catalyst which has particularly silver, an alkali metal activator, a rhenium activator, and an arbitrary rhenium coactivator deposited therein. Such an alkaline earth metal as mentioned above functions as a catalytic base in the absence of rhenium and forms an isomerizing active site in an excess quantity, with the result that the produced ethylene oxide will entail the problem of succumbing to successive oxidation and consequently lowering the selectivity.

JP-A-05–84440 discloses a catalyst characterized by having a catalytically effective quantity of silver, a promoting quantity of an alkali metal, and a promoting quantity of rhenium deposited on a carrier comprising at least 85 wt. % of α-alumina, 0.05–6 wt. % (determined as oxide MO) of an alkaline earth metal in the form of an oxide, 0.01–5 wt. % (determined as dioxide) of silicon in the form of an oxide, and 0 1–10 wt. % (determined as dioxide) of zirconia in the form of an oxide.

We have proposed a carrier for a catalyst obtained by using refractory inorganic particles as seeds and depositing a refractory inorganic powder and zirconia sol on the seeds and a method for the production thereof (JP-A-02–290257), a catalyst for the production of ethylene oxide using an α-alumina carrier having the outer surface of the carrier and the surface of pores in the carrier coated with amorphous silica (JP-A-02–194839), and a catalyst for the production of ethylene oxide using an α-alumina carrier having the outer surface of the carrier and the surface of pores in the carrier coated with amorphous silica-alumina (JP-A-05–329368).

Thus, the desirability of materializing further improvement of the selectivity, improvement of the activity, and long-time stabilization of the life performance has been finding enthusiastic popular approval.

These catalysts are excellent in catalytic performance and satisfactory to a certain extent from the industrial point of view. According to SRI published in January, 1997, the annual production of ethylene oxide in the whole world is about 12 million tons. The quantity of ethylene to be used as the raw material therefor is estimated to be about 9,500,000 tons when the selectivity of the catalyst used for the production of ethylene oxide is 80% or about 8,500,000 tons when the selectivity is 90%, indicating that an improvement of 10% in the selectivity results in saving about 1 million tons of ethylene annually in the world. Even such a minute improvement as 0.1% in the selectivity, therefore, brings a huge cost merit because this improvement permits a saving of about 10,000 tons of ethylene in the whole world.

When the reaction temperature of the catalyst to be used for the production of ethylene oxide is unduly high, the production requires the plant used therefor to satisfy a very high design pressure which some of the existing plants may possibly fail to meet. Further, since the high reaction temperature results in lowering the tolerable oxygen concentration for explosion limits and consequently heightening the degree of danger, the actual commercial operation of the plant is preferred to proceed at a temperature of not higher than 250° C. from the viewpoint of both performance and safety of the plant.

This invention, therefore, has for an object thereof the provision of a catalyst of the ethylene oxide production grade materializing preparation of a catalyst for the production of ethylene oxide excellent in catalyst properties, namely activity, selectivity, and life, a method for the production thereof, and a method for the production of ethylene oxide by the use of the catalyst.

SUMMARY OF THE INVENTION

The various objects mentioned above accomplished by the following items (1)–(3).

(1) A catalyst for the production of ethylene oxide, having silver deposited on a carrier which comprises 90.0–98.9 mass % of α-alumina, 0.01–1 mass % (calculated as oxide) of a compound of at least one metal selected from the group consisting of potassium and iron, 0.1–5 mass % (calculated as oxide) of a silicon compound, and 1–5 mass % (calculated as oxide) of zirconium compound.

(2) A method for the production of a catalyst set forth in the preceding item (1), characterized by depositing silver and an alkali metal on a carrier comprising 90.0–98.9 mass % of α-alumina, 0.01–1 mass % (calculated as oxide) of a compound of at least one metal selected from the group consisting of potassium and iron, 0.1–5 mass % (calculated as oxide) of a silicon compound, and 1–5 mass % (calculated as oxide) of zirconium compound in inner portion thereof, drying the resultant composite, and subjecting the dried composite to a heat treatment performed in the presence of an oxygen-containing gas at a temperature in the range of 60–450° C. and a heat treatment performed in the atmosphere of an inert gas at a higher temperature in the range of 450–700° C.

(3) A method for the production of ethylene oxide, characterized by effecting gas phase oxidation of ethylene with a molecular oxygen-containing gas by the use of a catalyst set forth in the item (1) or a catalyst produced by the method set forth in the item (2).

Since the catalyst contemplated by this invention for the production of ethylene oxide is possessed of such a construction as described above, it brings an improvement in the selectivity for ethylene oxide, an improvement in the activity, and an improvement in the long-time life performance as compared with the conventional countertype.

DESCRIPTION OF THE PREFERRED EMBODIMENT

The catalyst carrier contemplated by this invention for the production of ethylene oxide is prepared from α-alumina powder of high purity, a compound affording potassium oxide and/or iron oxide, silica sol, a compound affording zirconia (arbitrary components) and conventional binder/perfect combustion agent.

The α-alumina which is used for the preparation of the catalyst has an assay approximating to 98 mass %, preferably exceeding 98.5 mass % and has a sodium impurity content not exceeding about 0.06 mass %, specifically falling in the range of 0.02–0.06 mass %. The alumina comprises α-crystals having an average particle size preferably in the range of about 0.5—about 5 μm, preferably in the range of about 1—about 4 μm. These crystals are preferred to aggregate and form particles having an average particle diameter in the range of 30–100 μm, favorably in the range of 40–80 μm. The average size of such microcrystals has been decided by measuring the maximum sizes and the minimum sizes of a certain number of such microcrystals in the image of the transmission electron microscope (TEM) and averaging the results of the measurement. The α-alumina is present in the fired carrier in a quantity in the range of 90.0–98.9 mass %, preferably in the range of 92–97 mass %, based on the total mass of the carrier.

The BET (Brunauer-Emmett-Teller) specific surface area of the α-alumina powder is in the range of 0.1–5 m$^2$/g, preferably in the range of 0.5–4 m$^2$/g.

The quantity of the potassium and/or iron component (calculated as oxide, i.e. $K_2O$ and/or $Fe_2O_3$) in the composition of the carrier contemplated by this invention is in the range of 0.01–1 mass %, preferably in the range of 0.03—about 0.8 mass %, and more preferably in the range of 0.05–0.5 mass %, based on the total mass of the carrier. If the quantity of the metal falls short of 0.01 mass %, the shortage will result in preventing the incorporated metal from bringing a discernible improvement in the selectivity. Conversely, the quantity exceeds 1 mass %, the excess will result in degrading both the activity and the selectivity.

The potassium compound which can be used for the production of the carrier of this invention is such a compound as undergoes decomposition or forms an oxide during the process of calcination. Examples of the compound that answers this description include carbonates, nitrates, and carboxylates and further embrace the oxides of these salts, and mixed oxides of aluminates, silicates, and aluminosilicates. As typical examples of the compound, compounds such as potassium hydroxide and potassium oxide and natural products such as potassium feldspar. Among other compounds cited, potassium hydroxide and potassium oxide prove particularly advantageous.

The cationic species which is thought to contribute to the stabilization of an amorphous layer as a network modifier ion in the structure of amorphous silica is preferred to be an alkali metal, particularly potassium. Further, the iron compound is thought to make a specific contribution to the stabilization of an amorphous layer because iron exhibits specific selectivity to the carrier contemplated by this invention among other transition metal elements. When potassium and/or iron is contained, it is preferable to extrude a IIa element because potassium and/or iron induces degradation of performance due to the excessive promotion of the basic function inherent in the compound of a IIa element. The content of this IIa compound (as reduced to oxide, MO) preferably falls below 0.1 mass %, more preferably below 0.05 mass %, and most preferably below 0.01 mass %, based on the total mass of the carrier.

The silicon compound which is used in the production of the carrier contemplated by this invention is an oxide or a compound which is decomposable into an oxide in the process of calcination. Proper compounds answering this description include silicon dioxide itself and potassium silicate, zirconium silicate, and silica sol as well. Silica sol proves particularly advantageous. The compound content (calculated as $SiO_2$) in the final carrier composition is preferably in the range of about 0.1—about 5 mass %, more preferably in the range of about 0.03—about 5 mass %, and most preferably in the range of about 0.05—about 5 mass %.

Though zirconia is an arbitrary component, the quantity thereof is in the range of 1–5 mass %, preferably in the range of about 1.5—about 4.5 mass %, and particularly preferably in the range of about 2 —about 4 mass %, based on the total mass of the carrier. Where zirconia is formed in situ, the quantity of zirconia to be used ought to be so selected as to give a final ratio falling in the range specified above.

The zirconium compound which can be used in the production of the carrier contemplated by this invention is an oxide or a compound which is decomposable into an oxide in the process of calcination. The zirconium compounds answering this description include carbonates, nitrates, and carboxylates, for example. As typical examples of such proper compounds, zirconium nitrate, zirconia sol, zirconium dioxide, zirconium silicate, and such mixed oxides as zirconium alumino-silicate may be cited. Zirconia sol proves particularly advantageous among other compounds cited above.

The perfect combustion agent is a material which is so incorporated in the mixture that it may be perfectly removed from the carrier in the process of calcination and consequently enabled to leave controlled pores behind in the carrier. The materials answering this description include coke, carbon powder, graphite, powdered plastics (such as of polyethylene, polystyrene, and polycarbonate), rosin, cellulose and cellulosic materials, sawdust, and carbon-based materials such as ground fruit shells (such as shells of pecan, cashew, nut, and hazel nut), and other plant materials. A varying type of carbon-based binder also can serve as a perfect combustion agent. The perfect combustion agent is supplied in such a quantity and a size distribution as affords a final carrier exhibiting a pore volume preferably in the range of about 10–80 cc/g and more preferably in the range of 30–70 cc/g. A preferred perfect combustion agent is a material originating in the cellulose such as of ground hard fruit shell.

The term "binder" as used in the present specification means a so-called low-temperature binder, namely a reagent which is capable of retaining together the components of the carrier mentioned above and consequently forming an extrudable paste prior to the calcination thereof. This binder also facilitates the step of extrusion by imparting a lubricating property. Typical examples of the binder include a combination of alumina gel with such a peptizer as nitric acid or acetic acid. Suitable binders embrace such carbon-based materials are capable of acting as a perfect combustion agent. Typical examples of these binders, cellulose, substituted celluloses (such as methyl cellulose, ethyl cellulose, and carboxyethyl cellulose), organic stearic esters (such as, for example, methyl and ethyl stearates), waxes, and polyolefin oxides may be cited. Preferred binders are methyl cellulose and starch.

The components of the carrier obtained as described above are mixed and the resultant mixture is then formed in a prescribed shape such as, for example, pellets, rings, and spheres. The average equivalent diameter of these particulates is generally in the range of 3–20 mm and preferably in the range of 5–10 mm.

The formed product is dried to expel the water component which transforms to steam during the process of calcination and not to disrupt the physical cohesive property of the formed product. Typically, the drying operation and the calcination operation may be put together into one step by suitably programming time and temperature. The calcination is performed under conditions sufficient for removing the perfect combustion agent and the binder and causing the α-alumina particles to be fused into porous hard clusters. The calcination is typically performed in an oxidizing atmosphere such as, for example, oxygen gas or preferably the air at a highest temperature exceeding 1200° C., preferably falling in the range of about 1300°—about 1500° C. The duration of the calcination operation at this highest temperature may be in the range of about 0.5-about 300 minutes.

The specific surface area of the carrier for the catalyst contemplated by this invention is generally in the range of 0.05–10 m$^2$/g, preferably in the range of 0.1–5 m$^2$/g, and more preferably in the range of 0.2–2.0 m$^2$/g. If the specific surface area is unduly low, the shortage will result in preventing acquisition of a fully satisfactory coefficient of water absorption and rendering difficult the deposition of a catalyst component because the sintering proceeds excessively. Conversely, if the specific surface area is unduly high, the excess will result in decreasing the diameter of pores and promoting the secondary oxidation of ethylene oxide as the final product. The water absorption ratio is generally in the range of 10–70%, preferably in the range of 20–60%, and more preferably in the range of 30–50%. If the water absorption ratio is unduly low, the shortage will result in rendering the deposition of a catalyst component difficult. Conversely, if the water absorption ratio is unduly high, the excess will result in preventing the carrier from acquiring fully satisfactory strength. The mean pore diameter is generally in the range of 0.1–5 μm, preferably in the range of 0.2–3 μm, and more preferably in the range of 0.3–0.9 μm. If the mean pore diameter is unduly large, the excess will result in lowering the activity. Conversely, if the mean pore diameter is unduly small, the shortage will result in promoting the successive oxidation of ethylene oxide as the final produce owing to the stagnation of the gas. The porosity is generally in the range of 40–80% and preferably in the range of 50–70%. If the porosity is unduly low, the shortage will result in excessively enlarging the specific gravity of the carrier. Conversely, if the porosity is unduly high, the excess will result in preventing the carrier from acquiring fully satisfactory strength.

As the catalyst additive to the carrier contemplated by this invention, alkali metals are effective and cesium is most effective. Generally, the deposition of this additive on the carrier is effected by a method which comprises in impregnating the carrier in a solution of the additive. In the carrier of this invention, the addition of an element of VIa group and an element of VII group in the Periodic Table of the Elements is observed to tend to degrade both activity and selectivity.

The catalyst contemplated by this invention for the production of ethylene oxide can be prepared by following the method commonly used in the preparation of a catalyst for use in the production of ethylene oxide. The catalyst component to be deposited on the carrier may be silver alone or a combination of silver with a reaction promoter, namely an alkali metal such as, for example, cesium. The expression "deposit the silver component" as used in the present specification embraces the mode of depositing not only silver alone but also silver and a reaction promoter.

Preferably, the preparation of the catalyst is effected by preparing an aqueous solution solely containing a silver compound intended to form silver or containing this silver compound in combination with a complexing agent intended to form a silver complex optionally further with a reaction promoter, impregnating the carrier with the aqueous solution, and drying and heat-treating the impregnated carrier. The product of this heat treatment is preferred to be further subjected to a high-temperature heat treatment.

This drying can be carried out in the atmosphere of an oxygen-containing gas such as air or an inert gas such as nitrogen at a temperature in the range of 60°–120° C. It is particularly preferable to effect this drying in the atmosphere of an inert gas.

This heat treatment is preferred to be performed in the atmosphere of an oxygen-containing gas such as air or an inert gas such as nitrogen at a temperature in the range of 60°–450° C. Though it may be carried out in one step, it is preferred to be carried out in two or more steps. Particularly, the first step properly proceeds in the atmosphere of an oxygen-containing gas at a temperature in the range of 150°–250° C. for a duration in the range of 0.02–10 hours. Thereafter, the second step is properly performed in the atmosphere of an oxygen-containing gas at a temperature in the range of 250°–450° C. for a duration in the range of 0.02–10 hours.

The high-temperature heat treatment is preferred to proceed in the atmosphere of an inert gas selected from among nitrogen, helium, and argon at a temperature in the range of 450°–700° C. for a duration in the range of 0.1–10 hours.

As typical examples of the oxygen-containing atmosphere, the atmosphere of air and the atmosphere of a gas having an adjusted oxygen concentration may be cited.

As typical examples of the atmosphere of an inert gas, the atmosphere of an inert gas selected from among nitrogen, helium, and argon, the atmosphere of a reducing gas selected from between hydrogen and carbon monoxide, and the atmosphere of a mixed gas of an inert gas and a reducing gas may be cited.

As typical examples of the silver compound mentioned above, silver nitrate, silver carbonate, silver oxalate, silver acetate, silver propionate, silver lactate, silver citrate, and silver neodecanoate may be cited. As typical examples of the complexing agent, monoethanolamine, diethanolamine, triethanolamine, ethylene diamine, and propylene diamine may be cited. As typical examples of the rection promoter, alkali metals such as lithium, sodium, potassium, rubidium, and cesium, and thallium and sulfur may be cited. Among other reaction promoters cited above, alkali metals prove particularly advantageous. These reaction promoters may be used either singly or in the form of a combination of two or more members.

The catalyst contemplated by this invention for the production of ethylene oxide is preferred to have silver as a catalytic component and such a reaction promoter as cesium deposited on the carrier. The quantity of silver to be deposited is generally in the range of 1–30 mass %, preferably in the range of 5–20 mass % based on the total mass of the catalyst. When at least one element selected from the group consisting of alkali metals such as lithium, potassium, rubidium, and cesium and thallium is used as the reaction promoter, the total quantity of the reaction promoter is generally in the range of 0.0001–5 mass %, preferably in the range of 0.001–3 mass %, more preferably in the range of 0.01–2 mass %, and still more preferably in the range of 0.1–1 mass %, based on the total mass of the catalyst. If the coating ratio of silver manifested to the carrier is unduly low, the shortage will result in increasing the exposed surface of the carrier, bringing a consequent addition to the points of isomerizing activity which induces successive oxidation, and exerting an adverse effect on the selectivity. Conversely, if the coating ratio is unduly high, the excess will result in inducing enormous aggregation of silver during the course of the reaction.

The production of ethylene oxide by gas phase oxidation as contemplated by this invention may be implemented by following the method which has been in popular use heretofore excepting the aforementioned catalyst for the production of ethylene oxide is used for the purpose of catalysis.

Specifically, this method comprises preparing a raw material gas comprising 0.5–40 vol. % of ethylene, 3–10 vol. % of oxygen, 5–30 vol. % of carbon dioxide gas, and the balance of an inert gas such as nitrogen, argon, or steam and a lower hydrocarbon such as methane and ethane and further incorporating therein such an organic halogen compound as ethylene dichloride or ethyl chloride as a reaction inhibitor and advancing this raw material gas at a spatial velocity in the range of 1000–30000 $hr^{-1}$ (STP) and preferably in the range of 3000–8000 $hr^{-1}$ (STP) under a pressure in the range of 0.2–4 MPa and preferably in the range of 1.5–4 MPa at a temperature in the range of 180–300° C. and preferably in the range of 200–260° C. into contact with the aforementioned catalyst for the production of ethylene oxide.

Incidentally, the ethane content in the residual gas mentioned above is preferably not more than 3 vol. % and advantageously not more than 0.5 vol. %.

The organic halogen compound content in the residual gas is preferably not more than 100 ppm and advantageously not more than 10 ppm.

The reaction gas composed of 21 vol. % of ethylene, 7 vol. % of oxygen, 6 vol. % of carbon dioxide, 50 vol. % of methane, 14 vol. % of argon, 1.7 vol. % of nitrogen, 0.3 vol. % of ethane, and 3 ppm of ethyl chloride was fed to the catalyst. By feeding the gas to the catalyst for 100 hours at 3% of ethylene conversion based on the raw material gas, the average number of the mean silver particle on the catalyst decreased to 0.5–0.9 times the average number of the mean silver particle on the fresh catalyst. The decrease in the average number stabilizes the catalyst and consequently gives excellence in the life performance. This improvement of the catalyst may be logically explained by a supposition that the silver of this catalyst had such a morphology as fitted the factors including the carrier surface, the silver, and the reaction gas conditions.

Now, this invention will be described more specifically below with reference to working examples.

EXAMPLE 1

In a kneader, 94 parts by mass of α-alumina powder (A) (having an average crystal diameter of alumina of 1 μm, an average particle diameter of alumina of 65 μm, a BET specific surface area of 0.9 $m^2/g$, and a ratio of linear shrinkage of 15% after two hours' calcination at 1700° C.) (calculated as $Al_2O_3$), 4.5 parts by mass of zirconia sol (made by Nissan Chemicals Industries, Ltd. and sold under the product code of "NZS-30B") (as reduced to $ZrO_2$), 1.0 part by mass of silica sol (made by Nissan Chemicals Industries, Ltd. and sold under the product code of "Snowtex-N") (calculated as $SiO_2$), 0.2 part by mass of iron oxide (III) (made by Wako Pure Chemical Industries, Ltd. and sold under the product code of "99.9% Reagent") (calculated as $Fe_2O_3$), 0.1 part by mass of potassium hydroxide (made by Wako Pure Chemical Industries, Ltd. and sold under the product code of "Reagent Chemical") (calculated as $K_2O$), 6 parts by mass of methyl cellulose, 6 parts by mass of corn starch, and 30 parts by mass of ground nut shell (having an average particle diameter in the range of 100–170 μm) were introduced, thoroughly mixed, and further mixed thoroughly with 40 parts by mass of water added anew thereto. The resultant mixture was extrusion molded into rings, pelletized, dried, and calcined at 1400° C. for 2 hours to afford a carrier (A).

This carrier (A) was found to have an aluminum content of 94 mass % (carrier) calculated as $Al_2O_3$, a zirconium content of 4.5 mass % (carrier) calculated as $ZrO_2$, a silicon content of 1 mass % (carrier) calculated as $SiO_2$, an iron content of 0.2 mass % (carrier) calculated as $Fe_2O_3$, and a potassium content of 0.1 mass % (carrier) calculated as $K_2O$. It showed a BET specific surface area of 0.7 m²/g, a water absorption ratio of 44%, a mean pore diameter of 0.9 μm, and an apparent porosity of 65%.

The carrier obtained as described above was boiled and washed 3 times with purified water and dried. The quantity 210 g of the washed carrier was impregnated with a complex solution formed of 57.2 g of silver oxalate, 38.6 ml of ethylenediamine, 41.4 ml of water, and 0.22 g of cesium nitrate, then heated, concentrated, further dried at 120° C. for 30 minutes, then dried in draft at 150° C. for 30 minutes and at 300° C. for 30 minutes, then left cooling to normal room temperature, and further heat-treated in the atmosphere of nitrogen at 600° C. for 1 hour to afford a catalyst (a) for the production of ethylene oxide.

EXAMPLE 2

In a kneader, 94 parts by mass of α-alumina powder (A) (calculated as $Al_2O_3$), 4.5 parts by mass of zirconia powder (made by Wako Pure Chemical Industries, Ltd. and sold under the product code of "Reagent Chemical") (calculated as $ZrO_2$), 1.0 part by mass of silica sol (calculated as $SiO_2$), 0.2 part by mass of iron oxide (III) (calculated as $Fe_2O_3$), 0.1 part by mass of potassium hydroxide (calculated as $K_2O$), 6 parts by mass of methyl cellulose, 6 parts by mass of corn starch, and 30 parts by mass of ground nut shell (having an average particle diameter in the range of 100–170 μm) were introduced, thoroughly mixed, and further mixed thoroughly with 40 parts by mass of water added anew thereto. The resultant mixture was extrusion molded into rings, pelletized, dried, and calcined at 1500° C. for 2 hours to afford a carrier (B).

This carrier (B) was found to have an aluminum content of 94 mass % (carrier) calculated as $Al_2O_3$, a zirconium content of 4.5 mass % (carrier) calculated as $ZrO_2$, a silicon content of 1 mass % (carrier) calculated as $SiO_2$, an iron content of 0.2 mass % (carrier) calculated as $Fe_2O_3$, and a potassium content of 0.1 mass % (carrier) calculated as $K_2O$. It showed a BET specific surface area of 0.6 m²/g, a ratio of water absorption of 43%, a mean pore diameter of 1.0 μm, and an apparent porosity of 63%.

The carrier obtained as described above was boiled and washed three times with purified water and dried. The quantity 210 g of the washed carrier was impregnated with a complex solution formed of 57.2 g of silver oxalate, 38.6 ml of ethylene diamine, 41.4 ml of water, and 0.22 g of cesium nitrate, then heated, concentrated, further dried at 120° C. for 30 minutes, then dried in draft at 150° C. for 30 minutes and at 300° C. for 30 minutes, then left cooling to normal room temperature, and further heat-treated in the atmosphere of nitrogen at 600° C. for 1 hour to afford a catalyst (b) for the production of ethylene oxide.

EXAMPLE 3

In a kneader, 94 parts by mass of α-alumina powder (B) (having an average crystal diameter of alumina of 1 μm, an average particle diameter of alumina of 65 μm, a BET specific surface area of 2.1 m²/g, and a ratio of linear shrinkage of 14% after two hours' firing at 1700° C.) (calculated as $Al_2O_3$), 4 parts by mass of zirconia sol (calculated as $ZrO_2$), 1 part by mass of silica sol (calculated as $SiO_2$), 0.3 part by mass of iron oxide (III) (calculated as $Fe_2O_3$), 0.1 part by mass of potassium hydroxide (calculated as $K_2O$), 6 parts by mass of methyl cellulose, 6 parts by mass of corn starch, and 30 parts by mass of ground nut shell (having an average particle diameter in the range of 100–170 μm) were introduced, thoroughly mixed, and further mixed thoroughly with 40 parts by mass of water added anew thereto. The resultant mixture was extrusion molded into rings, pelletized, dried, and calcined at 1500° C. for 2 hours to afford a carrier (C).

This carrier (C) was found to have an aluminum content of 94 mass % (carrier) calculated as $Al_2O_3$, a zirconium content of 4 mass % (carrier) calculated as $ZrO_2$, a silicon content of 1 mass % (carrier) calculated as $SiO_2$, an iron content of 0.3 mass % (carrier) calculated as $Fe_2O_3$, and a potassium content of 0.1 mass % (carrier) calculated as $K_2O$. It showed a BET specific surface area of 1.2 m²/g, a ratio of water absorption of 40%, a mean pore diameter of 0.8 μm, and an apparent porosity of 61%.

The carrier obtained as described above was boiled and washed 3 times with purified water and dried. The quantity 210 g of the washed carrier was impregnated with a complex solution formed of 57.2 g of silver oxalate, 38.6 ml of ethylenediamine, 41.4 ml of water, and 0.22 g of cesium nitrate, then heated, concentrated, further dried at 120° C. for 30 minutes, then dried in draft at 150° C. for 30 minutes and at 300° C. for 30 minutes, then left cooling to normal room temperature, and further heat-treated in the atmosphere of nitrogen at 600° C. for 1 hour to afford a catalyst (c) for the production of ethylene oxide.

EXAMPLE 4

In a kneader, 94 parts by mass of α-alumina powder (B) (calculated as $Al_2O_3$), 4 parts by mass of zirconia sol (calculated as $ZrO_2$), 2 parts by mass of silica sol (calculated as $SiO_2$), 0.3 part by mass of iron oxide (III) (calculated as $Fe_2O_3$), 0.1 part by mass of potassium hydroxide (calculated as $K_2O$), 6 parts by mass of methyl cellulose, 6 parts by mass of corn starch, and 30 parts by mass of ground nut shell (having an average particle diameter in the range of 100–170 μm) were introduced, thoroughly mixed, and further mixed thoroughly with 40 parts by mass of water added anew thereto. The resultant mixture was extrusion molded into rings, pelletized, dried, and calcined at 1400° C. for two hours to afford a carrier (D).

This carrier (D) was found to have an aluminum content of 94 mass % (carrier) calculated as $Al_2O_3$, a zirconium content of 4 mass % (carrier) calculated as $ZrO_2$, a silicon content of 2 mass % (carrier) calculated as $SiO_2$, an iron content of 0.3 mass % (carrier) calculated as $Fe_2O_3$, and a potassium content of 0.1 mass % (carrier) calculated as $K_2O$.

It showed a BET specific surface area of 1.2 m²/g, a ratio of water absorption of 40%, a mean pore diameter of 0.8 μm, and an apparent porosity of 61%.

The carrier obtained as described above was boiled and washed 3 times with purified water and dried. The quantity 210 g of the washed carrier was impregnated with a complex solution formed of 57.2 g of silver oxalate, 38.6 ml of ethylenediamine, 41.4 ml of water, and 0.22 g of cesium nitrate, then heated, concentrated, further dried at 120° C. for 30 minutes, then dried in draft at 200° C. for 10 minutes and at 400° C. for 10 minutes, then left cooling to normal room temperature, and further heat-treated in the atmosphere of nitrogen at 500° C. for four hours to afford a catalyst (d) for the production of ethylene oxide.

EXAMPLE 5

In a kneader, 93 parts by mass of α-alumina powder (A) (calculated as $Al_2O_3$), 3 parts by mass of zirconia powder (calculated as $ZrO_2$), 3 parts by mass of silica sol (calculated as $SiO_2$), 0.3 part by mass of iron oxide (III) (calculated as $Fe_2O_3$), 0.1 part by mass of potassium hydroxide (calculated as $K_2O$), 6 parts by mass of methyl cellulose, 6 parts by mass of corn starch, and 30 parts by mass of ground nut shell (having an average particle diameter in the range of 100–170 μm) were introduced, thoroughly mixed, and further mixed thoroughly with 40 parts by mass of water added anew thereto. The resultant mixture was extrusion molded into rings, pelletized, dried, and calcined at 1500° C. for 2 hours to afford a carrier (E).

This carrier (E) was found to have an aluminum content of 93 mass % (carrier) calculated as $Al_2O_3$, a zirconium content of 3 mass % (carrier) calculated as $ZrO_2$, a silicon content of 3 mass % (carrier) calculated as $SiO_2$, an iron content of 0.3 mass % (carrier) calculated as $Fe_2O_3$, and a potassium content of 0.1 mass % (carrier) calculated as $K_2O$. It showed a BET specific surface area of 0.7 m²/g, a ratio of water absorption of 42%, a mean pore diameter of 0.8 μm, and an apparent porosity of 62%.

The carrier obtained as described above was boiled and washed three times with purified water and dried. The quantity 210 g of the washed carrier was impregnated with a complex solution formed of 57.2 g of silver oxalate, 38.6 ml of ethylene diamine, 41.4 ml of water, and 0.22 g of cesium nitrate, then heated, concentrated, further dried at 120° C. for 30 minutes, then dried in draft at 200° C. for 10 minutes and at 400° C. for 10 minutes, then left cooling to normal room temperature, and further heat-treated in the atmosphere of nitrogen at 550° C. for 3 hours to afford a catalyst (e) for the production of ethylene oxide.

EXAMPLE 6

In a kneader, 97 parts by mass of α-alumina powder (A) (calculated as $Al_2O_3$), 2 parts by mass of zirconia powder (calculated as $ZrO_2$), 0.5 part by mass of silica sol (calculated as $SiO_2$), 0.1 part by mass of iron oxide (III) (calculated as $Fe_2O_3$), 0.1 part by mass of potassium hydroxide (calculated as $K_2O$), 6 parts by mass of methyl cellulose, 6 parts by mass of corn starch, and 30 parts by mass of ground nut shell (having an average particle diameter in the range of 100–170 μm) were introduced, thoroughly mixed, and further mixed thoroughly with 40 parts by mass of water added anew thereto. The resultant mixture was extrusion molded into rings, pelletized, dried, and calcined at 1500° C. for 4 hours to afford a carrier (F).

This carrier (F) was found to have an aluminum content of 97 mass % (carrier) calculated as $Al_2O_3$, a zirconium content of 2 mass % (carrier) calculated as $ZrO_2$, a silicon content of 0.5 mass % (carrier) calculated as $SiO_2$, an iron content of 0.1 mass % (carrier) calculated as $Fe_2O_3$, and a potassium content of 0.1 mass % (carrier) calculated as $K_2O$. It showed a BET specific surface area of 0.5 m²/g, a ratio of water absorption of 39%, a mean pore diameter of 0.7 μm, and an apparent porosity of 59%.

The carrier obtained as described above was boiled and washed 3 times with purified water and dried. The quantity 210 g of the washed carrier was impregnated with a complex solution formed of 57.2 g of silver oxalate, 38.6 ml of ethylene diamine, 41.4 ml of water, and 0.22 g of cesium acetate, then heated, concentrated, further dried at 120° C. for 30 minutes, then dried in draft at 250° C. for 20 minutes and at 450° C. for 20 minutes, then left cooling to normal room temperature, and further heat-treated in the atmosphere of nitrogen at 600° C. for 1 hour to afford a catalyst (f) for the production of ethylene oxide.

EXAMPLE 7

In a kneader, 97 parts by mass of α-alumina powder (A) (calculated as $Al_2O_3$), 1.5 parts by mass of zirconia powder (calculated as $ZrO_2$), 1 part by mass of silica sol (calculated as $SiO_2$), 0.1 part by mass of iron oxide (III) (calculated as $Fe_2O_3$), 0.1 part by mass of potassium hydroxide (calculated as $K_2O$), 6 parts by mass of methyl cellulose, 6 parts by mass of corn starch, and 30 parts by mass of ground nut shell (having an average particle diameter in the range of 100–170 μm) were introduced, thoroughly mixed, and further mixed thoroughly with 40 parts by mass of water added anew thereto. The resultant mixture was extrusion molded into rings, pelletized, dried, and calcined at 1500° C. for 2 hours to afford a carrier (G).

This carrier (G) was found to have an aluminum content of 97 mass % (carrier) calculated as $Al_2O_3$, a zirconia content of 1.5 mass % (carrier) calculated as $ZrO_2$, a silicon content of 1 mass % (carrier) calculated as $SiO_2$, an iron content of 0.1 mass % (carrier) calculated as $Fe_2O_3$, and a potassium content of 0.1 mass % (carrier) calculated as $K_2O$. It showed a BET specific surface area of 0.5 m²/g, a ratio of water absorption of 42%, a mean pore diameter of 0.9 μm, and an apparent porosity of 62%.

The carrier obtained as described above was boiled and washed 3 times with purified water and dried. The quantity 210 g of the washed carrier was impregnated with a complex solution formed of 57.2 g of silver oxalate, 38.6 ml of ethylenediamine, 41.4 ml of water, and 0.22 g of cesium nitrate, then heated, concentrated, further dried at 120° C. for 30 minutes, then dried in draft at 150° C. for 30 minutes and at 300° C. for 30 minutes, then left cooling to normal room temperature, and further heat-treated in the atmosphere of nitrogen at 600° C. for 1 hour to afford a catalyst (g) for the production of ethylene oxide.

EXAMPLE 8

In a kneader, 97 parts by mass of α-alumina powder (A) (calculated as $Al_2O_3$), 1.5 parts by mass of zirconia sol (calculated as $ZrO_2$), 1 part by mass of silica sol (calculated as $SiO_2$), 0.1 part by mass of iron oxide (III) (calculated as $Fe_2O_3$), 0.1 part by mass of potassium hydroxide (calculated as $K_2O$), 6 parts by mass of methyl cellulose, 6 parts by mass of corn starch, and 30 parts by mass of ground nut shell (having an average particle diameter in the range of 100–170 μm) were introduced, thoroughly mixed, and further mixed thoroughly with 40 parts by mass of water added anew thereto. The resultant mixture was extrusion molded into rings, pelletized, dried, and calcined at 1500° C. for 2 hours to afford a carrier (H).

This carrier (H) was found to have an aluminum content of 97 mass % (carrier) calculated as $Al_2O_3$, a zirconium content of 1.5 mass % (carrier) calculated as $ZrO_2$, a silicon content of 1 mass % (carrier) calculated as $SiO_2$, an iron content of 0.1 mass % (carrier) calculated as $Fe_2O_3$, and a potassium content of 0.1 mass % (carrier) calculated as $K_2O$. It showed a BET specific surface area of 0.8 $m^2/g$, a ratio of water absoption of 41%, a mean pore diameter of 0.9 μm, and an apparent porosity of 61%.

The carrier obtained as described above was treated by following the procedure of Example 1 to afford a catalyst (h) for the production of ethylene oxide.

Control 1

A carrier (I) (having an aluminum content of 82 mass % (carrier) calculated as $Al_2O_3$, a zirconium content of 10 mass % (carrier) calculated as $ZrO_2$, a silicon content of 5 mass % (carrier) calculated as $SiO_2$, an iron content of 1.1 mass % (carrier) calculated as $Fe_2O_3$, a potassium content of 1.1 mass % (carrier) calculated as $K_2O$, a BET specific surface area of 0.9 $m^2/g$, a ratio of water absorption of 48%, a mean pore diameter of 1.5 μm, and an apparent porosity of 66%) was boiled and washed 3 times and dried. The quantity 210 g of the washed carrier was impregnated with a complex solution formed of 57.2 g of silver oxalate, 38.6 ml of ethylenediamine, 41.4 ml of water, and 0.22 g of cesium nitrate, then heated, concentrated, further dried at 120° C. for 30 minutes, then heated in draft at 150° C. for 30 minutes, heated at 300° C. for 30 minutes, then left cooling to normal room temperature, and further heat-treated in the atmosphere of nitrogen at 600° C. for 1 hour to afford a catalyst (i) for the production of ethylene oxide.

Control 2

A carrier (J) (having an aluminum content of 90 mass % (carrier) calculated as $Al_2O_3$, a zirconium content of 5 mass % (carrier) calculated as $ZrO_2$, a silicon content of 4 mass % (carrier) calculated as $SiO_2$, an iron content of 1.3 mass % (carrier) calculated as $Fe_2O_3$, a potassium content of 0.1 mass % (carrier) calculated as $K_2O$, a BET specific surface area of 0.9 $m^2/g$, a ratio of water absorption of 47%, a mean pore diameter of 1.5 μm, and an apparent porosity of 66%) was boiled and washed 3 times and dried. The quantity 210 g of the washed carrier was impregnated with a complex solution formed of 57.2 g of silver oxalate, 38.6 ml of ethylenediamine, 41.4 ml of water, and 0.22 g of cesium nitrate, then heated, concentrated, further dried at 120° C. for 30 minutes, then heated in draft at 150° C. for 30 minutes, heated at 300° C. for 30 minutes, then left cooling to normal room temperature, and further heat-treated in the atmosphere of nitrogen at 600° C. for 1 hour to afford a catalyst (j) for the production of ethylene oxide.

Control 3

A carrier (K) (having an aluminum content of 98 mass % (carrier) as reduced to $Al_2O_3$, a zirconium content of 0.5 mass % (carrier) calculated as $ZrO_2$, a silicon content of 0.5 mass % (carrier) calculated as $SiO_2$, an iron content of 0.3 mass % (carrier) calculated as $Fe_2O_3$, a potassium content of 1.1 mass % (carrier) calculated as $K_2O$, a BET specific surface area of 0.5 $m^2/g$, a ratio of water absorption of 38%, a mean pore diameter of 0.6 μm, and an apparent porosity of 57%) was boiled and washed 3 times and dried. The quantity 210 g of the washed carrier was impregnated with a complex solution formed of 57.2 g of silver oxalate, 38.6 ml of ethylene diamine, 41.4 ml of water, and 0.22 g of cesium nitrate, then heated, concentrated, further dried at 120° C. for 30 minutes, then heated in draft at 150° C. for 30 minutes, heated at 300° C. for 30 minutes, then left cooling to normal room temperature, and further heat-treated in the atmosphere of nitrogen at 600° C. for 1 hour to afford a catalyst (k) for the production of ethylene oxide.

EXAMPLE 9

The catalysts (a)–(k) were each crushed and sifted to separate a portion of 600–850 mesh. A reaction tube made of stainless steel and measuring 3 mm in inside diameter and 600 mm in length was packed with 1.2 g of the separated powder and was utilized for gas phase oxidation of ethylene under the following conditions. After 120 hours of the reaction continued with the degree of conversion of ethylene set at 3% based on the quantity of the raw material gas, the selectivity of the reaction for ethylene oxide and the reaction temperature of the catalyst bed were determined. The results are shown in Table 1.

| <Reaction conditions> | |
|---|---|
| Space velocity: | 6200 $hr^{-1}$ |
| Reaction pressure: | 2.1 MPa |
| Raw material gas: | 21 vol. % of ethylene, 7 vol. % of oxygen, 6 vol. % of carbon dioxide, 50 vol. % of methane, 14 vol. % of argon, 1.7 vol. % of nitrogen, 0.3 vol. % of ethane, 3 ppm of ethyl chloride |

TABLE 1

| Catalyst used | Selectivity (%) | Reaction temperature (° C.) |
|---|---|---|
| a | 81.7 | 237 |
| b | 81.3 | 242 |
| c | 82.2 | 222 |
| d | 82.1 | 225 |
| e | 81.5 | 243 |
| f | 81.4 | 245 |
| g | 81.9 | 233 |
| h | 81.5 | 240 |
| i | 79.8 | 272 |
| j | 79.6 | 268 |
| k | 80.0 | 263 |

What is claimed is:

1. A catalyst for the production of ethylene oxide, having silver deposited on a carrier containing 90.0–98.9 mass % of α-alumina, 0.01–1 mass % of a compound of at least one metal element selected from the group consisting of potassium and iron (calculated as oxide), 0.1–5 mass % of a silicon compound (calculated as oxide), and 1–5 mass % of zirconium compound (calculated as oxide).

2. A catalyst according to claim 1, wherein said carrier has a BET specific surface area in the range of 0.05–10 m²/g, a water absorption ratio in the range of 10–70%, a mean pore diameter in the range of 0.1–5 μm, and an apparent porosity in the range of 40–80%.

3. A catalyst according to claim 1, wherein the quantity of silver deposited is in the range of 1–30 mass %.

4. A catalyst according to claim 1, wherein at least one element selected from the group consisting of lithium, sodium, potassium, rubindium, and cesium is contained in a quantity such that the total content thereof is in the range of 0.0001–5 mass % (calculated as the oxide, $M_2O$) based on the total mass of the catalyst.

5. A catalyst according to claim 1, wherein the carrier is further deposited with cesium in the range of 0.01–1 mass % (calculated as the oxide, $M_2O$) based on the total mass of the catalyst.

6. A method for the production of a catalyst, which comprises depositing silver and an alkali metal on a carrier containing 90.0–98.9 mass % of α-alumina, 0.01–1 mass % of a compound of at least one metal element selected from the group consisting of potassium and iron (calculated as oxide), 0.1–5 mass % of a silicon compound (calculated as oxide), and 1–5 mass % of zirconium compound (calculated as oxide), drying the resultant composite, heat-treating the dried composite at a temperature in the range of 60°–450° C. in the presence of an oxygen-containing gas, and subjecting the heated composite to a high-temperature heat treatment in the atmosphere of an inert gas at a temperature in the range of 450°–700° C.

7. A method according to claim 6, wherein the heat treatment at 60°–450° C. in the presence of an oxygen-containing gas is carded out at not less than two steps.

8. A method for the production of ethylene oxide, characterized by subjecting ethylene to gas phase oxidation with a molecular oxygen-containing gas by the use of a catalyst, wherein the catalyst is a silver-deposited carrier containing 90.0–98.9 mass % of α-alumina, 0.01–1 mass % of a compound of at least one metal element selected from the group consisting of potassium and iron (calculated as oxide), 0.1–5 mass % of a silicon compound (calculated as oxide), and 1–5 mass % of zirconium compound (calculated as oxide).

9. A method according to claim 8, wherein said carrier has a BET specific surface area in the range of 0.05–10 m²/g, water absorption ratio in the range of 10–70%, a mean pore diameter in the range of 0.1–5 μm, and an apparent porosity the range of 40–80%.

10. A method according to claim 8, wherein the quantity of silver deposited is in the range of 1–30 mass %.

11. A method according to claim 8, wherein the carrier is further deposited with at least one element selected from the group consisting of lithium, sodium, potassium, rubidium, and cesium in a quantity such that the total content thereof is in the range of 0.0001–5 mass % (calculated as the oxide, $M_2O$) based on the total mass of the catalyst.

12. A method according to claim 8, wherein the carrier is further deposited with cesium in the range of 0.01–1 mass % (calculated as the oxide, $M_2O$) based on the total mass of catalyst.

13. A method according to claim 8, wherein the catalyst is produced by depositing silver and an alkali metal on the carrier, drying the resultant composite, heat-treating the dried composite at a temperature in the range of 60–450° C. in the presence of an oxygen-containing gas, and subjecting the heated composite to a high-temperature heat treatment in the atmosphere of an inert gas at a temperature in the range of 450°–700° C.

14. A method according to claim 13, wherein the heat treatment at 60–450° C. in the presence of an oxygen-containing gas is carried out at not less than two steps.

* * * * *